United States Patent [19]

Day et al.

[11] 4,288,367

[45] Sep. 8, 1981

[54] 2-CYANO-2-CARBOXY-3-AZABICYCLO[3.1.0-]HEXANE, HYDRATES, ESTERS, AND SALTS THEREOF

[75] Inventors: Janet A. Day; Robert J. G. Searle, both of Sittingbourne, England

[73] Assignee: Shell Oil Company, Houston, Tex.

[21] Appl. No.: 201,106

[22] Filed: Oct. 28, 1980

[30] Foreign Application Priority Data

Nov. 16, 1979 [GB] United Kingdom ............... 39782/79

[51] Int. Cl.³ .................... A01N 43/38; C07D 209/52
[52] U.S. Cl. .................................... 260/326.27; 71/95
[58] Field of Search .................................. 260/326.27

[56] References Cited

U.S. PATENT DOCUMENTS 4,235,921  11/1980  Achini et al. .................. 260/326.27

FOREIGN PATENT DOCUMENTS 2907668  9/1979  Fed. Rep. of Germany .......... 71/95

OTHER PUBLICATIONS

Kerr, Chem. Abstracts, vol. 87, Abstract No. 17311w(1977).

*Primary Examiner*—Alton D. Rollins

[57] ABSTRACT

2-cyano-2-carboxy-3-azabicyclo[3.1.0]hexane, hydrates, esters, and salts thereof, useful as pollen-suppressants.

1 Claim, No Drawings

2-CYANO-2-CARBOXY-3-AZABICYCLO[3.1.0]HEXANE, HYDRATES, ESTERS, AND SALTS THEREOF

DESCRIPTION OF THE INVENTION

It has been found that 2-cyano-2-carboxy-3-azabicyclo[3.1.0]hexane, of the formula

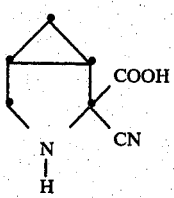

(I)

its hydrates, esters and salts, sterilize male anthers of plants, thus suppressing formation of pollen.

Suitable salts include the alkali metal and hydrohalide salts of the free acid, and hydrohalide salts of esters. Preferred are the alkyl esters having 1 to 4 carbon atoms in the alkyl group, and their hydrohalide salts.

Compounds of the invention can be prepared by treating the free acid of the formula II, or a hydrate, salt, or ester thereof

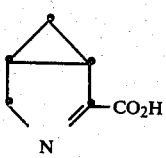

(II)

with hydrogen cyanide. In cases where a free acid of formula I, or a salt thereof is desired and an ester of the acid of formula II is used as starting material, hydrolysis and/or reaction of the ester with the appropriate acid or base effects the corresponding acid or salt thereof. In this regard, preferred starting materials are esters of the acid of formula II with alkanols of 1 to 4 carbon atoms.

The process is suitably carried out in the presence of an inert solvent, for example an alcohol, an ether such as diethyl ether, or a hydrocarbon or chlorinated hydrocarbon such as dichloromethane. A mixture of solvents may be used. The reaction temperature may for example be in the range of from $-10°$ to $60°$ C. For example, the reaction may be conducted at the reflux temperature of the solvent used. It is however most conveniently conducted at room temperature or slightly below, e.g. $0°$-$20°$ C.

It is preferable that the reaction be conducted under moisture-free conditions.

The molar ratio of the reactants may vary over a wide range. An excess of the hydrogen cyanide, for example up to a 5-fold, preferably up to a 3-fold, especially up to a 1.5 fold, excess, may be used.

The hydrogen cyanide may be generated in situ by the action of a strong mineral acid on an alkali metal cyanide, or by the use of a cyanohydrin under alkaline conditions, but it is preferably added as such, in the form of a gas, a solution in the reaction solvent, or, preferably, a liquid, to the compound of the general formula II.

The compounds of the invention exhibit both geometric and optical isomerism, depending on the relative positions of the substituents on the 2-carbon atom and the bridging methylene group. Depending on the reaction conditions used in their preparation certain isomers may be formed predominantly or exclusively. Compounds of the invention may be isomerised if desired by contacting the compound with a solvent in the presence of a compound containing, or capable under the reaction conditions of generating, free cyanide moieties. Under suitable conditions, this isomerisation may proceed close to the thermodynamic equilibrium of geometric isomers, which may if desired be separated from each other by any suitable method.

Esters of the acid of formula II may be prepared by oxidising an ester of the acid of the formula

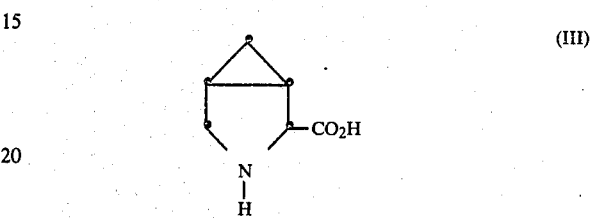

(III)

The oxidation may be carried out directly using an oxidising agent. Manganese dioxide is a suitable reagent, and the oxidation can be performed simply by stirring the ester of the compound of formula III with manganese dioxide in the presence of a suitable solvent, for example a hydrocarbon such as benzene or light petroleum. The reaction is conveniently performed at room temperature.

Alternatively, the oxidation may be carried out indirectly, for example by chlorinating or brominating an ester of the compound of formula III to give an ester of a compound of the general formula

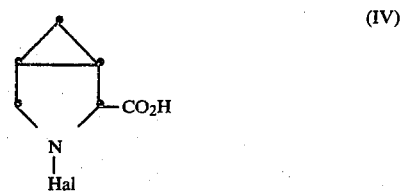

(IV)

in which Hal is a chlorine or bromine atom, and subsequently dehydrohalogenating the N-halo compound. The halogenation may be carried out using any suitable halogenating agent, for example N-bromo- or, especially, N-chlorosuccinimide, or an organic or inorganic hypohalite, for example t-butyl hypochlorite or sodium hypochlorite. Sodium hypochlorite may conveniently be used in the form of sodium hydroxide plus chlorine. The halogenation is suitably carried out by admixing the halogenating agent with an ester of the compound of the formula III. Any suitable solvent, for example an ether, may be used. The reaction may for example be carried out at a temperature in the range of from $-10°$ C. to $+30°$ C., the optimum temperature depending on the halogenating agent used. For example, if a hypohalite is used as halogenating agent, the reaction is preferably carried out at a temperature in the range of from $-10°$ C. to $+5°$ C., whereas if N-chlorosuccinimide is used as halogenating agent, the reaction is most conveniently carried out at room temperature.

Suitable dehydrohalogenating agents for the dehydrohalogenation step include organic bases and inorganic bases, for example an alkali metal hydroxide or alkoxide. Care should be taken however to ensure that the reaction conditions are such that the ester group is not attacked. For this reason, the base used should be relatively non-nucleophilic; for example, sodium ethoxide is generally to be preferred to sodium hydroxide. The reaction may be carried out in any suitable polar solvent, for example an ether or an alcohol, and is suitably carried out a temperature of up to 150° C., preferably at a temperature in the range 0° to 80° C.

Esters of the compound of formula III may be prepared by the method described in European Patent Application No. 79200034.

The acid starting material according to formula II or salt thereof, is suitably obtained by conversion of an ester of the acid according to formula II, prepared as described above, into the free acid II or salt thereof by hydrolysis. The hydrolysis may be carried out by any of the methods used for the hydrolysis of esters, for example using acidic or basic catalysts, and whether an acid or a salt is formed depends of course on the conditions. In a preferred embodiment of the process according to the invention the hydrolysis is carried out using water only, to avoid the introduction of inorganic ions into the reaction mixture. Such a procedure may facilitate work-up of the final product.

Alternatively, the free acid starting material may be obtained by direct oxidation of the acid whose carbon skeleton comprises the structure of formula III or a salt thereof or it may be converted indirectly by the process of N-chlorination or N-bromination followed by dehydrohalogenation as described above for the conversion of esters. Conditions for the direct oxidation or for the N-halogenation and subsequent dehydrohalogenation of an acid or salt are as described for esters, except the it may be preferable to work in a reaction medium which consists of or includes water.

Addition of hydrogen cyanide to the ester of the acid of formula II results in an ester of the acid of formula I. If the free acid or a salt thereof is required, the resulting ester may be hydrolysed under mild conditions which do not hydrolyse the cyano group. If such a step is desired, it is most convenient to choose as starting ester an ester which is very readily hydrolysed under mild conditions, for example a butyl ester, which can be hydrolysed in water containing a trace of acid.

Compounds of the invention sterilise the male anthers of plants, especially small-grain cereal plants, without substantially affecting female fertility. This makes it possible to produce $F_1$ hybrids of self-pollinating plants using a simple chemical treatment. The invention therefore provides a pollen-suppressing composition which comprises a compound of the general formula I or a hydrate, salt and/or an ester thereof together with a suitable carrier.

The invention further provides a method of sterilising the male anthers of a plant, which comprises applying to the plant a compound of the general formula I or a hydrate, salt and/or alkyl ester thereof or a pollen-suppressing composition containing such a compound. The invention also provides a method of producing $F_1$ hybrid seed which comprises cross-pollinating a plant which has been treated by the sterilising process according to the invention with a second plant of a different strain.

Preferably the active compound or composition is applied to a small-grain cereal plant, for example wheat or barley, when the plant is at a stage of growth between late tillering and emergence of the ear. The compound or composition is suitably applied at a dosage of active compound of from 0.05 to 2 kilograms/hectare, preferably 0.25 to 1 kilogram/hectare.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating agricultural compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3-10% w of a dispersing agent and, where necessary, 0-10% of stabiliser(s) and/or other additives such as penetrants or stickers. Dusts are usually formulated as a dust concentrate having a similar compositions to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-25% w active ingredient and 0-10% w of additives such as stabilisers, slow release modifiers and binding agents. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or the oil-in-water type, and may have a thick 'mayonnaise'-like consistency.

The compositions of the invention may also contain other ingredients, for example, other compounds possessing insecticidal, herbicidal or fungicidal properties.

The following Examples illustrate the invention. In each case the identities of the compounds involved were confirmed by appropriate chemical and spectral analyses.

EXAMPLE 1

Preparation of 2-cyano-2-isopropoxycarbonyl-3-azabicyclo[3.1.0]-hexane (1)

30 ml of liquid hydrogen cyanide was rapidly added drop-by-drop to a stirred and ice-cooled solution of 2 g of 2-isopropoxycarbonyl-3-azabicyclo[3.1.0]hex-2-ene in 50 ml of dry diethyl ether. The solution was stirred at 0° to 5° C. for 7 hours and then allowed to warm up to room temperature. The diethyl ether and residual hydrogen cyanide were blown off with nitrogen. The residue was taken up in diethyl ether, dried over sodium sulphate and evaporated down. An orange liquid was obtained; it was dissolved in chloroform and passed over an alumina column, eluting with chloroform. After the first 100 ml was collected, the next 300 ml was collected and evaporated down, to give 1 as a straw-colored liquid.

EXAMPLE 2

Preparation of 2-cyano-2-ethoxycarbonyl-3-azabicyclo[3.1.0]hexane (2)

2 was prepared by a method analogous to that described in Example 1, starting from 2-ethoxycarbonyl-3-azabicyclo[3.1.0]hex-2-ene.

EXAMPLE 3

Demonstration of pollen-suppressing activity

Spring wheat, variety Sicco, was propagated in a glass-house in 13 centimeter pots containing a loam-based compost. Supplementary lighting was provided by high-pressure mercury vapor lamps to give constant day length of 16 hours. The temperature was maintained at approximately 20° C.

The compound to be tested was formulated as an aqueous solution containing 0.1% Nonidet P 40 (trade mark) as wetting agent and 1% acetone to aid solubility. This formulation was diluted with water to various concentrations and sprayed onto plants to run-off. The plants were treated at the growth stage when the second node of the plant was just detectable.

At ear emergence but before anthesis, 5 heads from each treated pot were placed in cellophane bags to prevent crosspollination. At maturity, the bagged ears were harvested, and seed set was recorded and compared with untreated controls.

The results are shown in the following Table.

TABLE

| Compound of Example No. | Dosage (ppm) | Grain Set Inhibition (% of control) |
| --- | --- | --- |
| 1 | 200 | 22 |
|   | 1000 | 45 |
| 2 | 300 | 30 |

It can be seen that both the test compounds produced a considerable reduction in seed set compared with the untreated control, clearly illustrating the ability of the compounds to sterilise the male anthers of the wheat.

We claim:

1. A member selected from the group consisting of compound of the formula

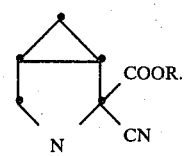

in which R is a hydrogen atom or alkyl of from 1 to 4 carbon atoms, the hydrates, and alkali metal salts of the acid, and the hydrochloride salts of the acid and esters.

* * * * *